(12) United States Patent
Patron Borbolla

(10) Patent No.: US 10,980,945 B1
(45) Date of Patent: Apr. 20, 2021

(54) SYRINGE AID

(71) Applicant: Liftie, LLC, Miami, FL (US)

(72) Inventor: Tanya Patron Borbolla, Miami, FL (US)

(*) Notice: Subject to any disclaimer, the term of this patent is extended or adjusted under 35 U.S.C. 154(b) by 137 days.

(21) Appl. No.: 16/241,651

(22) Filed: Jan. 7, 2019

(51) Int. Cl.
*A61M 5/31* (2006.01)

(52) U.S. Cl.
CPC ... *A61M 5/3137* (2013.01); *A61M 2005/3139* (2013.01)

(58) Field of Classification Search
CPC .............. A61M 5/3137; A61M 5/3148; A61M 2005/3139; A61M 2025/0266; A61M 2025/026; A61M 2025/0253; A61M 2025/0206
See application file for complete search history.

(56) References Cited

U.S. PATENT DOCUMENTS

| 5,833,668 | A | * | 11/1998 | Aguilar | ............... | A61M 5/3135 |
| | | | | | | 604/227 |
| 2012/0220948 | A1 | * | 8/2012 | Barbour | ............. | A61M 5/3137 |
| | | | | | | 604/189 |
| 2015/0238698 | A1 | * | 8/2015 | Perry | ................. | A61M 5/3137 |
| | | | | | | 604/227 |
| 2016/0199230 | A1 | * | 7/2016 | Doshi | ..................... | A61F 13/58 |
| | | | | | | 156/219 |

* cited by examiner

*Primary Examiner* — Phillip A Gray
(74) *Attorney, Agent, or Firm* — Christopher J. VanDam, PA; Chris Vandam

(57) ABSTRACT

A stretchy band that is placed over the plunger head of a syringe. The band is adhered to the underside of the plunger head. A thumb is snugly wrapped with the band to hold the thumb against the plunger head. The band is firmly secured around the thumb for operation of the syringe. A method of using this device is also disclosed.

9 Claims, 4 Drawing Sheets

SYRINGE AID

BACKGROUND OF THE INVENTION

1. Field of the Invention

The present invention relates to medical syringes, and more particularly, to a device and method of use to aid in operational use of a syringe.

2. Description of the Related Art

Several designs for syringe plunger devices and related have been designed in the past. None of them, however, include an openable band that tightly secures the thumb of the operator to the plunger head thereby allowing improved control and placement of the syringe during one handed operation and simultaneously improving the ability to precisely inject and aspirate the syringe.

Applicant believes that the closest reference corresponds to U.S. patent publication 2015/0238698 filed by Perry. However, it differs from the present invention because Perry lacks the features necessary to, among other things, adapt the band to any size syringe, does not tightly fit to any size thumb and does not adhere to the bottom side of the head making it less sanitary when available for re-use. Further, the Perry device could easily separate from the syringe risking injury to both the healthcare provider and the patient. Because Perry's device does not teach how to tightly fit to the administrator's thumb, the precision of the device is decreased over that of the presently claimed design.

Other patents describing the closest subject matter provide for a number of more or less complicated features that fail to solve the problem in an efficient and economical way. None of these patents suggest the novel features of the present invention.

A brief abstract of the technical disclosure in the specification and title are provided as well for the purposes of complying with 37 CFR 1.72 and are not intended to be used for interpreting or limiting the scope of the claims.

Without limiting the scope of the invention, a brief summary of some of the claimed embodiments of the invention is set forth below. Additional details of the summarized embodiments of the invention and/or additional embodiments of the invention may be found in the detailed description of the invention below.

SUMMARY OF THE INVENTION

It is one of the main objects of the present invention to provide a syringe aid with a thumb strap that adapts universally to any size syringe head.

It is another object of this invention to provide a syringe aid that tightly connects the user's thumb to the head of the syringe to increase precision when holding and using the syringe.

It is still another object of the present invention to provide a device that improves on the safety of both the patient and the healthcare provider when using a syringe.

Another object of the present invention is to create a device that encourages single use to improve hygienic conditions. The device and the syringe to which it is attached may be both disposable and discarded together after a single use.

It is yet another object of this invention to provide such a device and method for administering syringes that is inexpensive to manufacture and maintain while retaining effectiveness.

Further objects of the invention will be brought out in the following part of the specification, wherein detailed description is for the purpose of fully disclosing the invention without placing limitations thereon.

These and other embodiments which characterize the invention are pointed out with particularity in the claims annexed hereto and forming a part hereof. However, for a better understanding of the invention, its advantages and objectives obtained by its use, reference can be made to the drawings which form a further part hereof and the accompanying descriptive matter, in which there are illustrated and described various embodiments of the invention.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
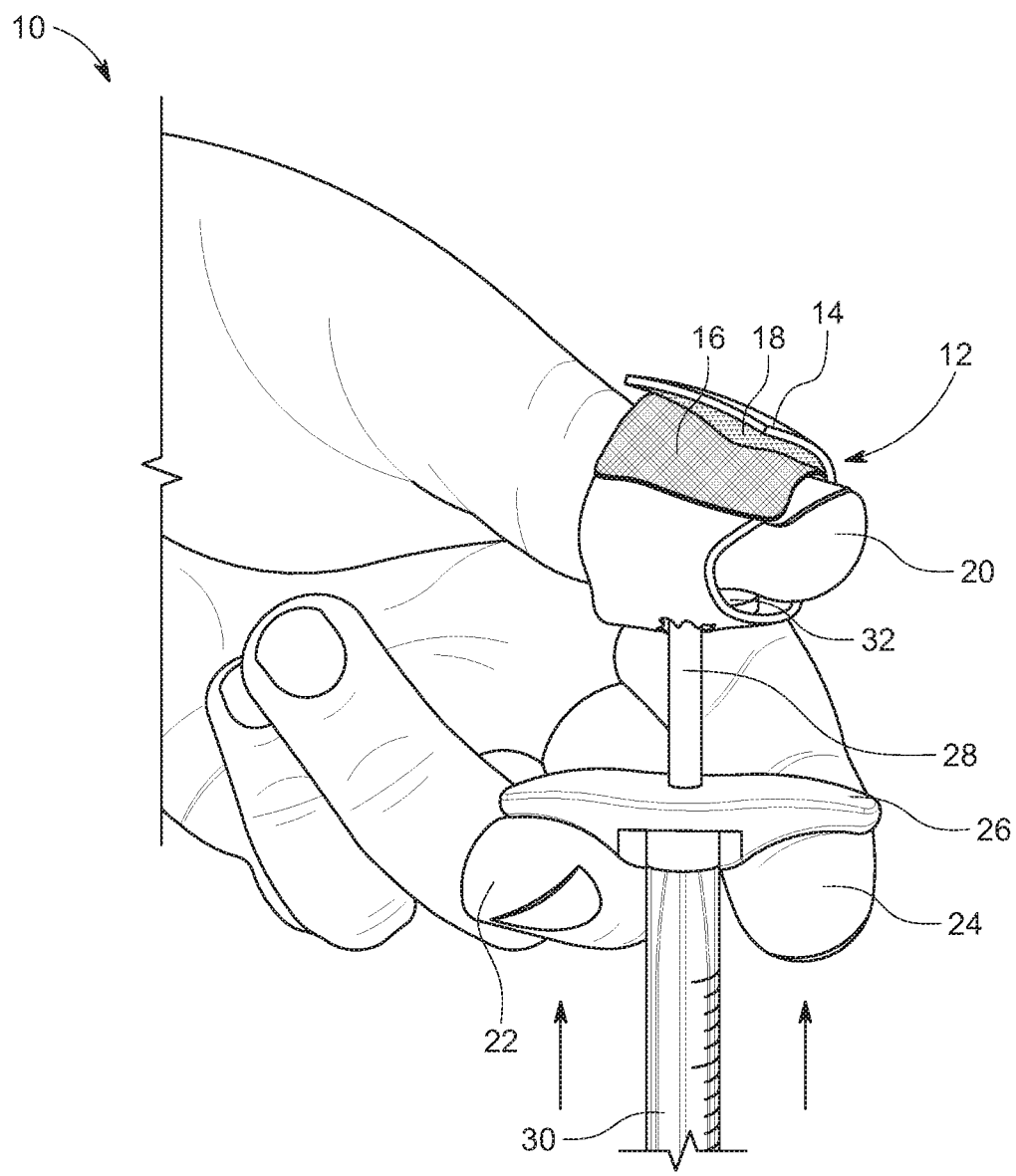
FIG. 1 shows a perspective view of a hand using a syringe in an injection mode.

While this invention may be embodied in many different forms, there are described in detail herein specific embodiments of the invention. This description is exemplary of the principles of the invention and is not intended to limit the invention to the particular embodiments illustrated and described.

For the purpose of this disclosure, like reference numerals in the figures shall refer to like features unless otherwise indicated or is obvious by context.

The subject device and method of use is sometimes referred to as the device, the method, the process, the invention, the band, the syringe, the strap, the machine or other similar terms. These terms may be used interchangeably as context requires and from use the intent becomes apparent. The masculine can sometimes refer to the feminine and neuter and vice versa. The plural may include the singular and singular the plural as appropriate from a fair and reasonable interpretation in the situation.

Referring now to the drawings, where the present invention is generally referred to with numeral 10, it can be observed that it basically includes a band assembly 12, a band 14, a fastener 16, a fastener 18, a thumb 20, a finger 22, a finger 24, a flange 26, a plunger 28, a barrel 30, a head 32, a slit 34, a reinforcement 36, an adhesive 38, an aperture 40, a tip 42, a surface 44 and a surface 46.

Figure 3:
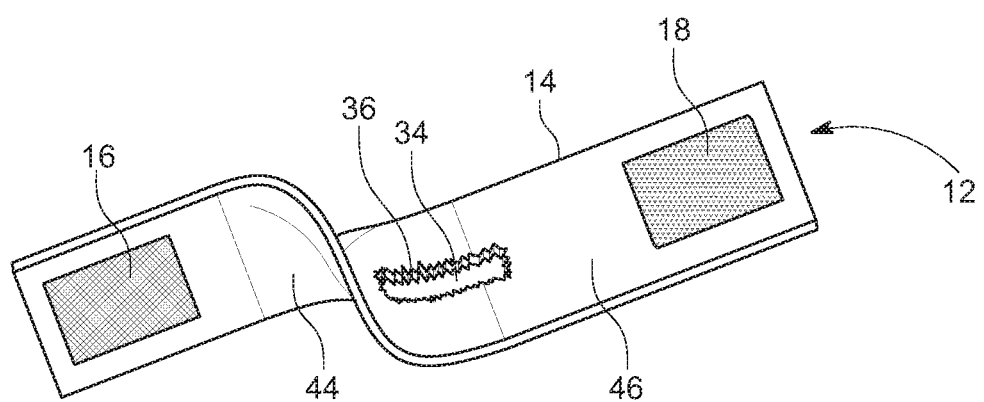
FIG. 3 shows a perspective view of a band assembly twisted to demonstrate optional and required features on both top and bottom surfaces.
Figure 4:
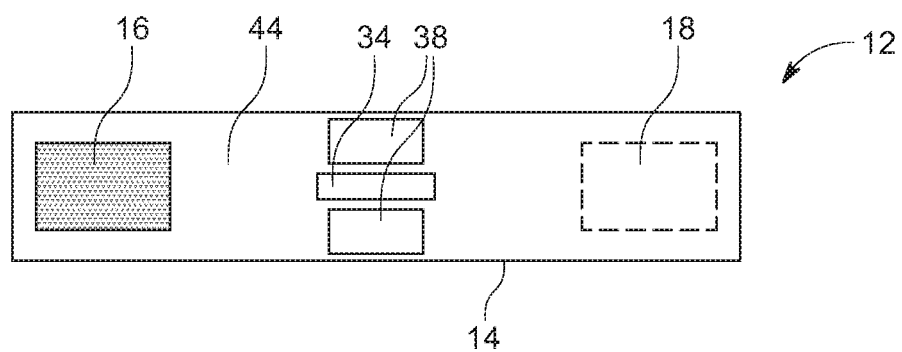
FIG. 4 shows a plan view of a band assembly demonstrating optional and required features.

FIGS. 3 and 4 show the general structure of the syringe aid that includes optional and necessary elements. The drawings are stylized and intended to show general features. Precise dimensions cannot be directly extrapolated. FIG. 3 is a similar version of the syringe aid as seen in FIG. 4. Some features in FIGS. 3 and 4 are optional and only appear in some versions of the invention.

The band assembly 12 includes a band 14 that is generally a thin layer and rectangular in shape. The band 14 preferably has elastic qualities that allow for longitudinal elongation when encircling a thumb 20. The band 14 should be flexible and able to readily conform the shape around a human thumb 20.

The band 14 may be made from a fabric material with an incorporated elastic material to allow for elongation and springing back around the thumb 20 of the user. Some fabric materials have inherent stretch without the need for multi-material construction. For example, synthetic woven or non-woven fabrics and layers may be suitable for construction of the band 14. Plastic films and laminates may also have sufficient stretch to firmly be secured to the thumb 20.

In one version of the invention, the band 14 generally will elongate by stretching about ten to fifty percent in overall length from its unstretched state. The device has been shown to be effective with a stretch factor of about two percent to over one hundred percent of length. The stretch across the short dimension of the band 14 is less critical but still is a factor for comfort.

However, in some versions a nearly unstretchable fabric may be used for the band 14 that allows a secure attachment around the thumb of the user. In this version the band may be made of a traditional fabric, fabric of other flexible material with limited stretch. Other versions may allow significantly more stretching ability of the band 14, for example, for wrapping more than one time around the thumb 20.

The band 14 may flex in both long and short directions to comfortably conform to the shape of the thumb 20. A soft material will avoid or reduce chafing or other discomfort. A band 14 made of absorbent material may slip less by avoiding accumulation of perspiration, condensation, medication or other slippery substance that gets on or near the band 14.

Figure 5:
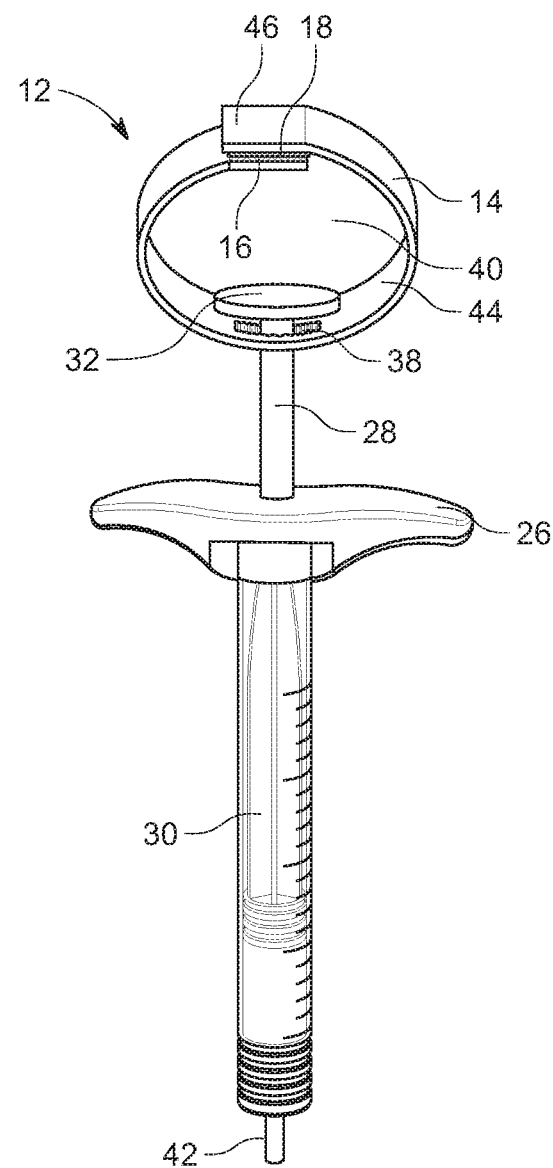
FIG. 5 shows a perspective view of a band assembly connected to a syringe.

Looking at FIG. 5, showing the band assembly 12 attached to a syringe, in combination with the isolated band assembly 12 in FIGS. 3 and 4 it can be appreciated that the band assembly 12 attaches to the plunger 28 below the head 32 of the syringe. The slit 34 is placed over the head 32 and around the plunger 28.

The slit 34 is formed into the band 14 in a central region of the band assembly 12. The slit 34 may parallel to the long axis of the band 14, perpendicular to the long axis or at any other angle in between. The orientation of the slit 34 may depend on the nature and configuration of the reinforcement 36 and/or adhesive 38, if either are present on a particular version of the design.

The slit 34 completely penetrates the band 14 so that the head 32 can pass entirely through the slit 34 and the plunger 28 can be through the band 14. To this end, the slit 34 is dimensioned to be fit over the head 32 of the syringe and around the plunger 28. Generally, the length of the slit 34 is about a half centimeter to about two and a half centimeters. An important version of the syringe aid that fits a commonly used type of cosmetic syringe has a slit 34 between approximately one to one and a half centimeters long.

Optionally, the slit 34 is bounded by a reinforcement 36. This maintains the integrity and dimensions of the slit 34. The reinforcement 36 may be stitching similar to a buttonhole stitch on a garment or another supporting structure. For example, the reinforcement could be an applied layer of adhesive, a cured material that bonds to the band 14 around the periphery of the slit 34 or other reinforcing element or member surrounding all or part of the slit 34.

The reinforcement 36, in at least one version of the design, has limited stretchability sufficient to be manipulated over the head 32 of the syringe yet resilient enough to not easily slip off of the head 32 during use of the syringe.

On one side of the band 14 is surface 46 that has affixed near an end the fastener 18. On the opposing side of the band 14 is surface 44 that has affixed near an end the fastener 16. In the version of the design shown in FIGS. 3-5 the fastener 16 is on the opposite surface 44 from the fastener 18 on surface 26. The fastener 16 and fastener 18 are also on opposite ends of the band 14 so that when the band 14 is looped around a thumb 20 the fastener 16 can engage and connect to fastener 18.

The fasteners 16 and 18 could be any features that can connect to each other to close the band 14 into a circle around the thumb 20. For example, the fasteners 16 and 18 could be hook and loop style pads, one each on the surface 44 and surface 46, respectively. An advantage of the hook and loop is that the band 14 can be tightened around a variety of thumb sizes. The user could also elect to tighten or loosen the band 14 around the thumb 20 to any degree that they wish for comfort purposes or to enhance dexterity and performance.

The fasteners 16 and 18 could also be fabricated from an adhesive section on either or both areas labeled fasteners 16 and 18 on FIGS. 3 and 4. In this version the adhesive section could be covered by a tab, such as a waxed paper, that is removed immediately prior to use when preparing the device for wrapping around a thumb 20. This could create a permanent bond forming the loop of the band 14 where the adhesive is not readily detached.

Similarly, a less aggressive adhesive section could be used for either or both fasteners 16 and 18, near where those elements appear on FIGS. 3 and 4. A less sticky adhesive could have its disposable protective cover removed and then applied to form the band 14 into a ring around the thumb 20 and then later adjusted and/or removed to loosen or tighten the band 14 around the finger as desired by the user based on their preferences.

In the case of any adhesive being used for either a removable or permanent fastener 16 or 18, only one or the other may need to be sticky and the other of the pair may have a place for the other corresponding part to be adhered. For example, fastener 18 may be the sticky part on the band and where faster 16 appears could be a landing area for the sticky fastener 18. In this example, the roles of fastener 16 and landing spot for the adhesive 18 section could be reversed and remain effective.

The fasteners 16 and 18 could be also be other types of effective connection means. For example, magnetic elements such as a pair of magnets or a magnet and a part that is attracted to a magnet. Other types of clips, snaps, binders or other things commonly known to attach the ends of the band 14 looped around a thumb 20 could be used to tightly connect the thumb 20 to the head 32 of a plunger 28 on a syringe for use in medical or clinical procedures.

The fastener 16 and 18 types disclosed herein may benefit from being non-separable so that the syringe aid must be discarded after a single use. For the removable or adjustable types of fasteners 16 and 18, like the magnets or hook and loop variety, the other adhesive 38 feature may limit reuse. For example, the adhesives 38 at one or both sides of the slit 34 may be non-removable from the underside of the head 32 once initially attached and thereby also cause the syringe aid to effectively be a single use device because it could not be readily attached to a new or different syringe prior use in another procedure.

As a practical matter, a one use syringe aid improves safety by improving hygiene. Many of the pre-filled syringes are intended to be single use and the single use syringe aid should preferably also be only used one time. The elastic nature of the band 14 could acquire contaminants like any other surface in a medical theater. The modest cost of the device suggests that it should be discarded with the attached syringe after use.

An adhesive 38 section may be around the slit 34 on the surface 44 of the band 14 that touches the underside of the head 32. There are two adhesive 38 sections shown in FIG. 4, one on either side of the slit 34. However, having a single unified adhesive 38 section, or only on one side of the slit 34, is also sufficient to connect the band 14 to the syringe head 34 permanently. Once the adhesive 38 is removed from the head 32 after a use neither the syringe aid or the syringe should be used again to maintain sterility.

Figure 2:
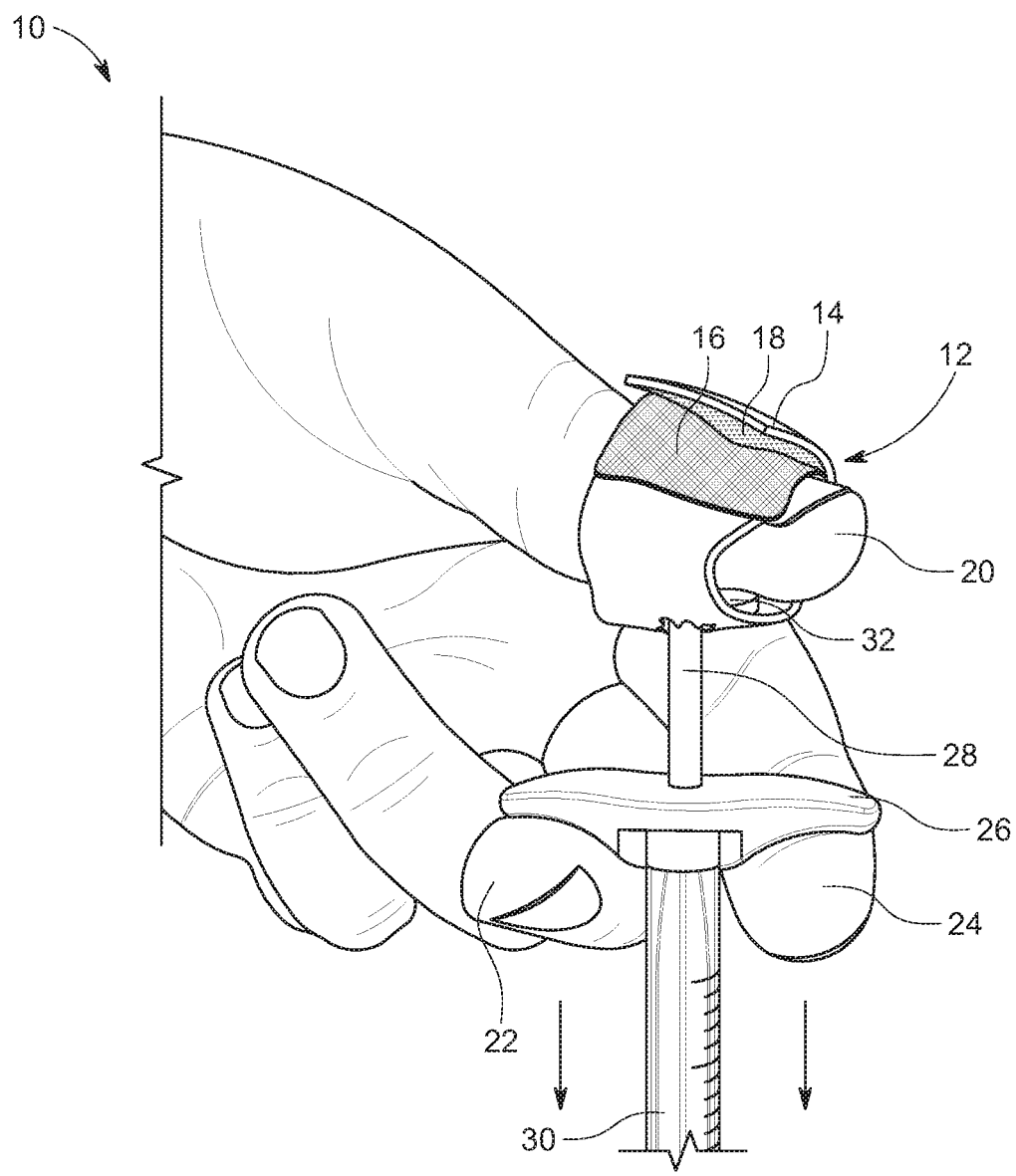
FIG. 2 shows a perspective view of a hand using a syringe in an aspiration mode.

Looking at FIGS. 1 and 2 where use of the syringe aid is demonstrated. It can generally be appreciated that the band assembly 12 is wrapped tightly around the thumb 20 to connect the thumb 20 to the head 32 of the syringe. In this manner the syringe can be held when only contacting the thumb 20. The syringe cannot be dropped or accidentally slip out of the users hands because it is connected to around the thumb 20 with the band 14.

FIG. 1 shows the thumb 20 wrapped in the syringe aid and connected to the head 32. The finger 22 and finger 24 are under the flange 26 and are positioned to squeeze the plunger 28 into the barrel 30 of the syringe to expel material out from the syringe. The thumb 20 contracts towards the flange 26 and is compressed with the fingers 22 and 24 in the injection phase of operation.

In the injection mode of operation shown in FIG. 1 there is little stress placed on the syringe aid. All of the force is derived from the thumb 20 pressing on the head 32 pinching against the finger 22 and finger 24 pressing against the bottom side of the flange 26 to dispense the contents of the barrel 30.

The user of the syringe aid can safely aspirate down to the last drop of the barrel 30, as it is shown in FIG. 2. With the strap secure, it allows the user to pull back on the plunger 28 without moving their grip or changing positions in grip thus making it more stable during aspiration and a safer injection by keeping the needle in the proper tissue plane. In other words the user can keep their fingers under the flange 26 even while aspirating and does not need to move them above the flange 26. Simply adducting the thumb is the only motion needed to aspirate since the thumb is secured to the device.

In FIG. 2 the opposite action is shown where an aspiration movement is demonstrated. In this mode, the finger 22 and finger 24 are placed under the flange 26 so that the pads of the finger 22 and finger 24 can press against the flange 26. In this mode the finger 22 and 24 hold on to the side of the barrel 30.

In FIG. 2 the muscles of the thumb 20 tend to force against the top of the band 14 pulling the head 32 away from the flange 26. Simultaneously the finger 22 and finger 24 oppose the thumb 20 to separate the flange 26 from the head 32 in the direction indicated by the arrows in FIG. 2 to draw material into the syringe through the tip 42 (shown in FIG. 5) in an aspiration action.

In some medical procedures the recommended technique for injections require a first aspiration through the hypodermic syringe to confirm whether the tip of needle is in a blood vessel or is in other non-vascular subcutaneous tissue. There are a variety of established procedures that require verification of the nature of the tissue into which the needle is located.

For example, with dermal fillers it would be dangerous to the patient to accidentally inject into the veins or arteries of the patient. The contents of the filler syringe could then travel to other locations in the body and cause a variety of undesirable effects. The healthcare provider should instead make sure that the injection is made safely into the non-vascular surrounding tissue.

By inserting the hypodermic needle and then first using an aspiration motion, as shown in FIG. 2, the user determines whether free flowing blood can easily be aspirated. If blood is drawn into the barrel 30 it can be surmised that a vein or artery has been pierced and therefore the injection motion shown in FIG. 1 should not proceed at that precise location on the patient's body.

If, on the other hand, when preparing for a filler injection, the aspiration mode demonstrated in FIG. 2 does not readily draw blood into the barrel 30 of the syringe then it has been determined that the tip of the hypodermic needle is in a safer position in the flesh of the patient and that the injection may proceed.

The above example is merely one procedure that the present syringe aid may be effectively employed. Aspiration techniques are not the only benefit of the present design. By having the thumb 20 tightly held onto the head 32 of the plunger 28 the healthcare provider can control the location of the needle with improved dexterity and therefore improve accuracy in placement of the needle. This applied to both the location of the injection and the depth of the injection.

In certain circumstances, such as in a procedure that may cause a reaction to the injection, the improved control of the syringe may also benefit both the patient and the healthcare provider. For example, if a patient may recoil from sensitivity from the injection, the better control of the syringe improves the results.

Further, by having the head 32 attached to the thumb 20 the operator of the syringe can control it with one hand better. Previously, using the syringe to aspirate required either loose fitting thumb rings and often a second hand to steady the syringe for aspiration or other delicate procedures. The present device and methods of its use solves these issues completely.

It should be appreciated that the drawings and description show an exemplary use. In some uses, and with some users, other digits or finger may be used. This can include those with missing or partially missing fingers. Further, those with limited use of the fingers because of illness or injury can find benefit with the present device and method of use by continuing the ability to use a syringe with the syringe aid and retaining proficiency of the device. In this sense the terms thumb, finger and digit may all be interchangeable depending on the use of the device and the particular user of the device.

A version of the present invention can be fairly described as a syringe aid comprised of a band having a first surface and a second surface, essentially a top and a bottom surface. A slit completely penetrates a central segment of the band completely through the first and second surface. The slit, in some respects similar to a button hole, is dimensioned to snugly fit over a preselected head of a syringe plunger. At a first end of the band on the first surface is a first fastener and at a second end of the band on the second surface is a second fastener. The fasteners could be any of complementary hook and loop fastener pads, at least one adhesive pad connected to the opposing end of the band, magnets, clips or clasps. On the second surface of the band adjacent to the slit is an adhesive adapted to permanently adhere the band to a bottom side of the head of the syringe plunger. The band is dimensioned so that when the band forms a loop and the first fastener engages the second fastener that the loop snugly and tightly, yet comfortably, fits a preselected human digit so that it is held against the syringe head during operation of the syringe. Generally, the band has the capability of stretching longitudinally between about ten and fifty percent of its unstretched length but could be as low as one percent or up to about one hundred percent of its length. A reinforcement may optionally be integrated with the band that surrounds a periphery of the slit. This strengthens the integrity of the slit and keeps it from tearing or coming off of the head. Some of these features may be added or removed to obtain the described performance.

The inventive concept also encompasses a method of using a syringe aid comprising, among other steps in no specific order, placing a slit in a band over a head of a plunger. Remove a protective cover (i.e. plastic or waxed paper) from an adhesive pad adjacent to the slit in the band to expose the adhesive pad. Then, adhering the adhesive pad to an underside of a plunger head so they stick together and are generally permanently joined. Wrap the band snugly around a thumb so that the thumb is held against a top side of the plunger head. Affix a first end of the band to a second end of the band to secure the band snugly around the thumb. Dispense a syringe by abducting (i.e. squeezing together) the thumb to a finger on an underside of a flange (to squeeze out the contents of the syringe through the tip) and alternately aspirating the syringe by adducting (i.e. separating apart) the thumb from the finger on a under side of the flange (to draw fluid into the barrel of the syringe through the tip).

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A syringe aid comprised of a band having a first surface and a second surface;
    a slit completely penetrates a central segment of the band completely through the first and second surface without bisecting an edge of the band;
    the syringe is comprised of a syringe plunger with a head;
    the slit in the band stretches to fit over and retain the head of the syringe plunger through the slit;
    at a first end of the band on the first surface is a first fastener;
    at a second end of the band on the second surface is a second fastener;
    on the second surface of the band adjacent to the slit is an adhesive adapted to adhere to a bottom side of the head of the syringe plunger;
    the band is dimensioned so that when the band forms a loop and the first fastener engages the second fastener that the loop snugly fits a preselected human digit.

2. The syringe aid in claim 1 further characterized in that the band stretches longitudinally between ten and fifty percent of its unstretched length.

3. The syringe aid in claim 1 further characterized in that a reinforcement is integrated with the band that surrounds a periphery of the slit.

4. The syringe aid in claim 1 further characterized in that the fasteners are complimentary hook and loop pads.

5. The syringe aid in claim 1 further characterized in that at least one of the fasteners is an adhesive pad.

6. A syringe aid comprised of a band having a first surface and a second surface;
    the band stretches longitudinally between ten and fifty percent of its unstretched length;
    a slit completely penetrates a central segment of the band completely through the first and second surface without bisecting an edge of the band;
    a reinforcement is integrated with the band that surrounds a periphery of the slit;
    the syringe is comprised of a syringe plunger with a head;
    the slit in the band stretches to fit over and retain the head of the syringe plunger through the slit;
    at a first end of the band on the first surface is a first fastener;
    at a second end of the band on the second surface is a second fastener;
    the fasteners are either complimentary hook and loop pads or at least one of the fasteners is an adhesive pad;
    on the second surface of the band adjacent to the slit is an adhesive adapted to adhere to a bottom side of the head of the syringe plunger;
    the band is dimensioned so that when the band forms a loop and the first fastener engages the second fastener that the loop snugly fits a preselected human digit.

7. A method of using a syringe aid comprising:
    placing a slit in a band completely over and around a head of a plunger;
    removing a cover from an adhesive pad adjacent to the slit in the band;
    adhering the adhesive pad to an underside of the plunger head;
    wrapping the band snugly around a thumb so that the thumb is held against a top side of the plunger head;
    affixing a first end of the band to a second end of the band to secure the band snugly around the thumb;
    dispensing a syringe by abducting the thumb to a finger on an underside of a flange and aspirating the syringe by adducting the thumb from the finger on the under side of the flange.

8. The method of using the syringe aid in claim 7 further characterized in that the band stretches between five and fifty percent of its length when wrapping the band snugly around the thumb.

9. The method of using the syringe aid in claim 7 further characterized in that first end of the band is affixed to the second end of the band with a hook and loop fastener or an adhesive pad.

* * * * *